United States Patent
Cain

(10) Patent No.: US 10,213,564 B2
(45) Date of Patent: Feb. 26, 2019

(54) BIOMEDICAL AURAL DELIVERY SYSTEMS AND METHODS

(71) Applicant: Frank J. Cain, Naples, FL (US)

(72) Inventor: Frank J. Cain, Naples, FL (US)

(*) Notice: Subject to any disclaimer, the term of this patent is extended or adjusted under 35 U.S.C. 154(b) by 218 days.

(21) Appl. No.: 14/712,334

(22) Filed: May 14, 2015

(65) Prior Publication Data

US 2015/0328413 A1 Nov. 19, 2015

Related U.S. Application Data

(60) Provisional application No. 62/000,322, filed on May 19, 2014.

(51) Int. Cl.
*A61M 11/00* (2006.01)

(52) U.S. Cl.
CPC ..... *A61M 11/00* (2013.01); *A61M 2205/3379* (2013.01); *A61M 2205/3592* (2013.01); *A61M 2205/50* (2013.01); *A61M 2205/8206* (2013.01); *A61M 2205/8237* (2013.01); *A61M 2205/8268* (2013.01); *A61M 2205/8275* (2013.01); *A61M 2205/8293* (2013.01); *A61M 2210/0662* (2013.01)

(58) Field of Classification Search
CPC ......... A61N 1/00; A61M 5/142; A61M 5/145; A61M 11/00; A61M 2210/0662; H04R 2460/15; A61F 11/002; A61F 2002/183
See application file for complete search history.

(56) References Cited

U.S. PATENT DOCUMENTS

| | | | | |
|---|---|---|---|---|
| 5,356,430 A | * | 10/1994 | Nadol, Jr. | A61F 2/18 623/10 |
| 5,364,838 A | * | 11/1994 | Rubsamen | A61K 9/007 514/5.9 |
| 5,421,818 A | * | 6/1995 | Arenberg | A61F 11/00 604/20 |
| 5,674,196 A | * | 10/1997 | Donaldson | A61M 3/0262 604/174 |
| 5,683,676 A | * | 11/1997 | Akehurst | A61K 31/522 222/635 |
| 5,713,847 A | | 2/1998 | Howard, III et al. | |
| 5,744,166 A | | 4/1998 | Illum | |
| 6,186,141 B1 | * | 2/2001 | Pike | A61B 18/12 128/203.12 |
| 6,251,138 B1 | * | 6/2001 | Nadol, Jr. | A61F 11/002 623/10 |

(Continued)

FOREIGN PATENT DOCUMENTS

WO WO2010126586 11/2010

OTHER PUBLICATIONS

PCT Search and Patentability Report for PCT/US2015/030788, dated Aug. 19, 2015.

*Primary Examiner* — Bhisma Mehta
*Assistant Examiner* — Matthew A Engel
(74) *Attorney, Agent, or Firm* — Remenick PLLC

(57) ABSTRACT

Inner ear treatment delivery devices and methods are disclosed. The device includes a pressurized container filled with a content, a control mechanism within the pressurized container, a nozzle coupled to the control valve, a microprocessor adapted to operate the control valve, and a power source providing energy to the device. The device administers at least one dose of the content to a patient's inner ear.

22 Claims, 1 Drawing Sheet

(56) References Cited

U.S. PATENT DOCUMENTS

| | | | |
|---|---|---|---|
| 6,358,231 B1* | 3/2002 | Schindler | A61F 11/00 604/1 |
| 6,969,383 B2 | 11/2005 | Hildebrand | |
| 7,206,639 B2 | 4/2007 | Jacobsen et al. | |
| 7,380,550 B2* | 6/2008 | Sexton | A61M 15/0065 128/200.14 |
| 7,815,615 B2 | 10/2010 | Jolly et al. | |
| 8,091,545 B2 | 1/2012 | Schechter et al. | |
| 8,202,260 B2 | 6/2012 | Mann et al. | |
| 8,409,152 B2* | 4/2013 | Hair | A61M 3/0262 128/200.14 |
| 8,452,392 B2* | 5/2013 | Morriss | A61M 1/0088 604/21 |
| 8,827,946 B2* | 9/2014 | Tsutsui | A61K 9/0043 604/212 |
| 8,840,602 B2* | 9/2014 | Morriss | A61F 11/00 604/21 |
| 9,180,054 B2* | 11/2015 | Fiering | A61F 11/002 |
| 2001/0043708 A1* | 11/2001 | Brimhall | H04R 25/456 381/328 |
| 2003/0097121 A1* | 5/2003 | Jolly | A61M 5/14276 604/891.1 |
| 2003/0229333 A1 | 12/2003 | Ashton | |
| 2003/0229336 A1* | 12/2003 | Jacobsen | A61F 11/00 604/890.1 |
| 2004/0172005 A1 | 9/2004 | Arenberg et al. | |
| 2006/0030837 A1* | 2/2006 | McKenna | A61F 11/00 604/890.1 |
| 2006/0050914 A1* | 3/2006 | Urso | H04R 25/656 381/328 |
| 2006/0253087 A1* | 11/2006 | Vlodaver | A61F 11/00 604/275 |
| 2007/0051362 A1* | 3/2007 | Sullivan | A61F 9/0008 128/200.23 |
| 2008/0009836 A1* | 1/2008 | Fiering | A61F 11/002 604/891.1 |
| 2008/0253583 A1* | 10/2008 | Goldstein | H04R 1/1091 381/92 |
| 2008/0262468 A1* | 10/2008 | Clifford | A61F 11/002 604/501 |
| 2009/0163890 A1* | 6/2009 | Clifford | A61B 1/227 604/514 |
| 2009/0209945 A1 | 8/2009 | Lobl et al. | |
| 2010/0198135 A1* | 8/2010 | Morriss | A61F 11/00 604/21 |
| 2011/0311462 A1* | 12/2011 | Eilat | A61K 9/0046 424/45 |
| 2012/0024724 A1* | 2/2012 | Beardsall | B08B 17/00 206/205 |
| 2012/0296268 A1* | 11/2012 | Vlodaver | A61F 11/00 604/43 |
| 2013/0035660 A1 | 2/2013 | Anand | |
| 2013/0053823 A1* | 2/2013 | Fiering | A61M 5/14276 604/514 |
| 2013/0144370 A1 | 6/2013 | Debruyne et al. | |
| 2013/0282075 A1 | 10/2013 | De Ridder | |
| 2013/0310805 A1* | 11/2013 | Yadidi | A61M 11/00 604/514 |
| 2014/0238774 A1* | 8/2014 | Blendinger | H04R 25/656 181/135 |
| 2015/0328413 A1* | 11/2015 | Cain | A61M 11/00 128/200.23 |
| 2017/0026732 A1* | 1/2017 | Kirsch | H04R 1/1041 |
| 2017/0143946 A1* | 5/2017 | Martin | A61M 31/00 |

* cited by examiner

BIOMEDICAL AURAL DELIVERY SYSTEMS AND METHODS

REFERENCE TO RELATED APPLICATIONS

This application claims priority to U.S. Provisional Application Ser. No. 62/000,322, filed May 19, 2014, entitled "Biomedical Aural Delivery Systems and Methods," which is hereby specifically and entirely incorporated by reference.

BACKGROUND

1. Field of the Invention

The invention is directed systems and methods of delivering medication to a patient's ear. Specifically, the invention is directed to systems and methods of non-invasively delivering medication to the inner ear.

2. Background of the Invention

The human ear has three main sections, which consist of the outer ear, the middle ear, and the inner ear. Sound waves enter the outer ear and travel through the ear canal to the middle ear. The ear canal channels the waves to the eardrum (or tympanic membrane), a thin, sensitive membrane stretched tightly over the entrance to the middle ear. The waves cause the eardrum to vibrate, which in turn passes the vibrations on to the hammer, one of three tiny bones in the ear. The hammer vibrating causes the anvil, the small bone touching the hammer, to vibrate. The anvil passes these vibrations to the stirrup, another small bone which touches the anvil. From the stirrup, the vibrations pass into the inner ear. The stirrup touches a liquid filled sack and the vibrations travel into the cochlea, which is shaped like a shell. Inside the cochlea, there are hundreds of special cells, called stereocilia, attached to nerve fibers, which can transmit information to the brain. The brain processes the information from the ear. FIG. 1 depicts a basic diagram of the human ear.

As acoustic sensors in mammals, stereocilia are lined up in the Organ of Corti within the cochlea of the inner ear. In hearing, stereocilia transform the mechanical energy of sound waves into electrical signals for the hair cells, which ultimately leads to an excitation of the auditory nerve. Stereocilia are composed of cytoplasm with embedded bundles of cross-linked actin filaments. The actin filaments anchor to the terminal web and the top of the cell membrane and are arranged in grade of height. When the stapes (the stirrup-shaped bone in the inner ear) causes sound waves in the endolymphatic fluid in the cochlea, the stereocilia are deflected in a shearing motion, which results in electrical signal for the hair cell.

In the inner ear, stereocilia are the mechanosensing organelles (structures with specialized functions, suspended in the cytoplasm of a cell) of hair cells, which respond to fluid motion in numerous types of animals for various functions, including hearing and balance. They are about 10-50 micrometers in length and share some similar features of microvilli. The hair cells turn the fluid pressure and other mechanical stimuli into electric stimuli via the many microvilli that make up stereocilia rods. Stereocilia exist in the auditory and vestibular systems.

Auditory dysfunctions are common. Various situations or medical conditions of the inner ear require the administration of drugs or like medicines to the middle ear. Such medical conditions or inner ear disorders can include sudden neurosensory hearing loss, Meniere's disease, and tinnitus. For example, in the United States, the prevalence of tinnitus when the whole population is considered is approximately 3%. This prevalence is only 1% under the age of 45 but increases significantly with age, rising to 9% in the population over 65 years. Tinnitus is a noise in the ears, often described as ringing, buzzing, roaring, or clicking. Subjective and objective forms of tinnitus exist, with objective tinnitus often caused by muscle contractions or other internal noise sources in the area proximal to auditory structures. In certain cases, external observers can hear the sound generated by the internal source of objective tinnitus. In subjective forms, tinnitus is audible only to the subject. Tinnitus varies in perceived amplitude, with some subjects reporting barely audible forms and others essentially deaf to external sounds and/or incapacitated by the intensity of the perceived noise. It has also been reported that, although the deaf cannot hear, they can experience tinnitus.

Typical devices for providing treatment to inner ear afflictions are implanted in the body and have a reservoir of medication that is dispensed into the inner ear to treat the symptoms. These devices are highly invasive, require surgery to implant, and then must be removed via surgery once the treatment is over. The invasive nature of the devices leads to the increased possibility of infection or that the patient's body may reject the device. Therefore, it is desirable to have a non-invasive device for treating inner ear conditions.

SUMMARY OF THE INVENTION

The present invention overcomes the problems and disadvantages associated with current strategies and systems and provides new systems and methods of non-invasively treating inner ear conditions.

One embodiment of the invention is directed to an inner ear treatment delivery device. The device comprises a pressurized vessel containing a substance, a control valve within the pressurized vessel, a nozzle coupled to the control mechanism, a microprocessor adapted to operate the control mechanism, and a power source providing energy to the device.

Preferably, the device is capable of emitting at least one amount of the substance to a patient's inner ear. In a preferred embodiment, the device is non-invasively insertable and removable from a patient's ear canal. The substance preferably diffuses through a patient's ear drum to the patient's inner ear.

The device preferably further comprises an external controller in communication with the microprocessor. Preferably, the external controller is one of a smart phone application or a dedicated device. Preferably, external controller is programmable to control dosage timing and amount. In a preferred embodiment, external controller is adaptable to instruct the device to provide a dose on demand.

The substance is preferably a vapor, a gas, or a liquid. Preferably the substance is a liquid and the nozzle atomizes the liquid upon emission of the liquid from the device. The pressurized vessel is preferably refillable and the nozzle is adapted to receive and emit the substance.

Another embodiment of the invention is directed to a method of treating an inner ear affliction. The method comprises the steps of providing a device having a pressurized vessel, a control mechanism, a nozzle, a microprocessor, and a power source, filling the pressurized vessel with a substance, inserting the device into a patient's ear canal, and instructing the device to administer at least one amount of the substance to the patient's inner ear.

Preferably, device is non-invasively insertable and removable from the patient's ear canal. Preferably, the substance diffuses through the patient's ear drum to the patient's inner ear. In a preferred embodiment, the step of instructing the device to administer at least one amount of the substance to the patient's inner ear is accomplished by an external controller in communication with the microprocessor.

Preferably, the external controller is one of a smart phone application or a dedicated device. The external controller is preferably programmable to control dosage timing and amount. In a preferred embodiment, external controller is adaptable to instruct the device to provide a dose on demand.

Preferably, the substance is a vapor, a gas, or a liquid. Preferably, the substance a liquid and further comprising atomizing the liquid upon emission of the liquid from the device. In a preferred embodiment, the pressurized vessel is refillable and the nozzle is adapted to receive and emit the substance.

Other embodiments and advantages of the invention are set forth in part in the description, which follows, and in part, may be obvious from this description, or may be learned from the practice of the invention.

DESCRIPTION OF THE DRAWINGS

The invention is described in greater detail by way of example only and with reference to the attached drawings, in which.

DESCRIPTION OF THE INVENTION

As embodied and broadly described herein, the disclosures herein provide detailed embodiments of the invention. However, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention.

Figure 1:
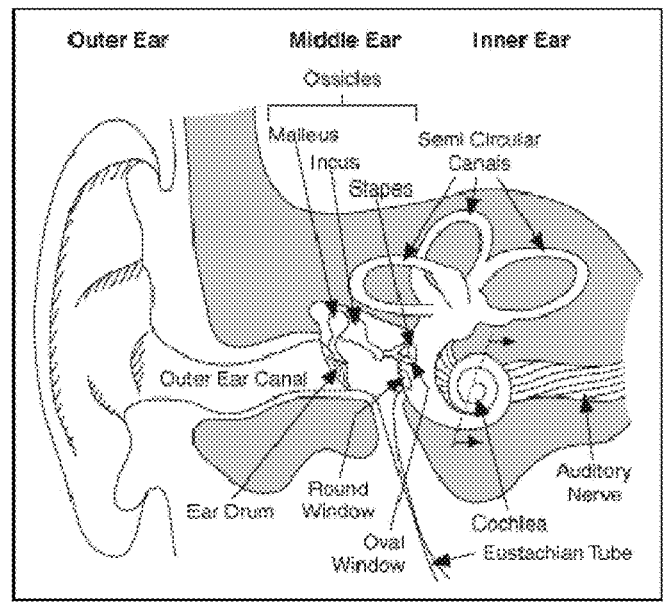
FIG. 1 is a basic schematic of a human ear.
Figure 2:
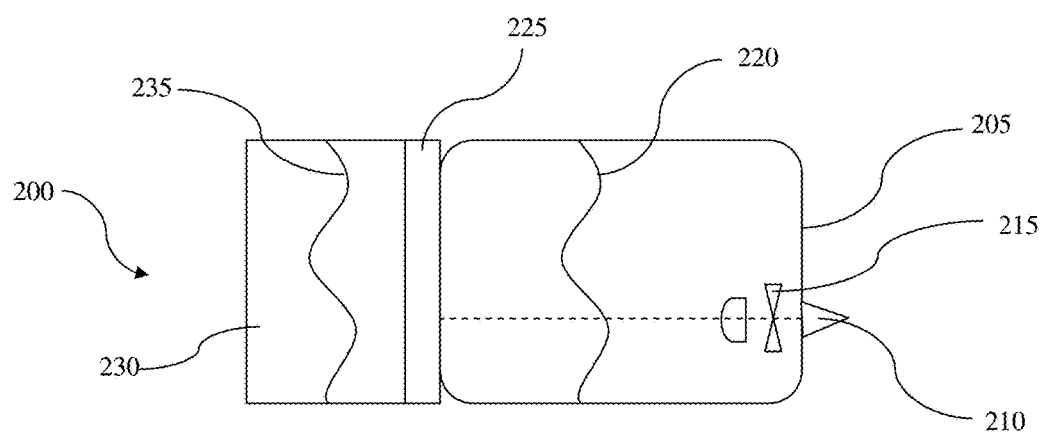
FIG. 2 depicts one embodiment of the medication delivery device.

FIG. 2 depicts an embodiment of the medication delivery device 200. This device provides a treatment for otoacoustic emissions resulting from damage to inner ear audio receptor cells (inner hair cells with stereocilia) that vibrate and outer hair cells that convert the signals into tension on a vibrating membrane. The resulting sounds are one of a number of possible causes of tinnitus. The etiology of tinnitus is unknown but may be a result of damage to the receptor cells and may be accompanied by hearing loss. The device may also be used to treat other conditions in the inner ear, such as non-auditory diseases, particularly inner ear infections and Meniere's disease.

Preferably, device 200 is sized and shaped to fit within the ear canal of a human (although the device may be used on other animals). Device 200 is a non-invasive device. Preferably device 200 is insertable and removable from the ear canal without penetrating or piercing the body of the patient. Preferably, device 200 is not implanted. Preferably, device 200 can be inserted into either ear and two devices can be inserted into both ears simultaneously. Device 200 can be held within the ear canal by friction, adhesive, or another non-invasive method.

Preferably, device 200 is has a universal size and shape to fit into the majority of ears. However, device 200 can come in various sizes and/or shapes, for example to fit within various sized ear canals or for children and adults. Furthermore, device 200 can be custom molded for each patient. Preferably, the entirety of device 200 is capable of fitting within the ear canal. In other embodiments, device 200 may protrude from the ear canal or only a portion of device 200 may be inserted into the ear canal. Preferably device 200 is molded to fit within the ear canal. However, device 200 can be cylindrical or have another shape. For example, the majority of the components of device 200 may be contained in a housing positioned behind the patient's ear and the delivery nozzle may be inserted into the ear to avoid blocking sound from entering the ear canal and disrupting hearing. Preferably, device 200 is waterproof or water resistant.

In the preferred embodiment, device 200 is a self-contained device. The device preferably includes a pressurized container (or vessel) 205, a fill/delivery nozzle 210, a control mechanism 215, a microprocessor 225, a power source 230, and a controller. The device may further include flexible seals 220 and 235 to prevent blowback, mitigate any leakage, and protect the components from external elements. In certain embodiments, device 200 may be coupled to a hearing aid and be capable of using the hearing aid's power source and/or microprocessor. Device 200 in combination with a hearing aid may mitigate hearing loss due to the device being placed within the ear canal.

Pressurized container 205 is preferably positioned so that when device 200 is inserted into the ear, pressurized container is adjacent to the ear drum. However, in other embodiments, pressurized container 205 can have other positions. Pressurized container 205 is preferably adapted to hold liquid or gas under pressure. For example pressurized container 205 may be capable of withstanding between 10 and 1000 psi of pressure, preferably between 20 and 500 psi, and more preferably between 30 and 100 psi. Preferably, pressurized container has a capacity of less than one milliliter, preferably between 1 and 500 microliters, and more preferably between 50 and 100 microliters of contents. Preferably, pressurized container 205 is made of plastic, however, pressurized container 205 can be made of glass, metal, fabric, or another manmade or naturally occurring material, or a combination thereof.

Preferably, pressurized container 205 is hypoallergenic and does not react with its contents. The inner or outer surface of pressurized container 205 may be coated to prevent reactions. Pressurized container 205 is preferably refillable or rechargeable, however pressurized container 205 may be prefilled and replaceable. Preferably, pressurized container 205 is filled with a medication capable of diffusing through the ear drum into the inner ear. As the ear drum is a membrane, many fluids and gasses are capable of diffusing through the membrane. Preferably, the contents are in gaseous or vapor form. For example, pressurized container 205 may be filled with one or more of $O_2$, $N_2$, $CO_2$, $NO_3$, $H_E$, $A_R$, antibiotics, and medical gasses. Preferably, the contents are administered in one or more therapeutically effective doses. The therapeutically effective does and concentration of the contents preferably can be determined by one of skill in the art through empirical testing.

Pressurized container 205 preferably contains a control mechanism 215. For example, control mechanism 215 may be a control valve. Control mechanism 215 is preferably adapted to release a specified amount of the contents of pressurized container 205. Control mechanism 215 preferably releases the contents through nozzle 210. Nozzle 210 is preferably positioned at an end of pressurized container 205 such that nozzle 210 touches, is adjacent to, or is in near proximity to the ear drum. In the preferred embodiment, control mechanism 215 and nozzle 210 are capable of being used to fill pressurized container 205 and delivering doses (or amounts) of the contents of pressurized container 205. In other embodiments, pressurized container 205 may have a separate fill valve and control mechanism 215 and/or nozzle 210 are one way devices. Nozzle 210 may be capable of atomizing the contents of pressurized container 205, for example if the contents are a liquid.

In the preferred embodiment, control mechanism 215 is controlled by microprocessor 225. Preferably, microprocessor 225 is positioned outside pressurized container 205 and in communication with control mechanism 215. For clarity of explanation, the illustrative system embodiment is presented as comprising individual functional blocks (including functional blocks labeled as a "microprocessor"). The functions these blocks represent may be provided through the use of either shared or dedicated hardware, including, but not limited to hardware capable of executing software. For example the functions of one or more microprocessors presented in FIG. 2 may be provided by a single shared microprocessor or multiple microprocessors. (Use of the term "microprocessor" should not be construed to refer exclusively to hardware capable of executing software.) Illustrative embodiments comprise microprocessor and/or digital signal processor (DSP) hardware, read-only memory (ROM) for storing software performing the operations discussed below, and random access memory (RAM) for storing results. Very large scale integration (VLSI) hardware embodiments, as well as custom VLSI circuitry in combination with a general purpose DSP circuit, may also be provided.

Preferably, microprocessor 225 opens and closes control mechanism 215 to emit a micro dose of the stored medication. For example, microprocessor 225 may instruct control mechanism 215 to emit between 1 and 500 microliters, preferably between 1 and 100 microliters, and more preferably between 1 and 20 microliters of the stored substance. Preferably, microprocessor 225 is programmable to vary the amount of the micro dosage and the number of doses that can be release in a period of time (e.g. per hour, 24 hours, or number of days). Preferably, microprocessor 225 and device 200 are powered by power source 230. Power source 230 can be a rechargeable battery, a replaceable battery, mechanically powered, solar powered, electrochemically powered, bio-electrically powered, powered by the patient's body (e.g. movement or heat), or another power source. In certain embodiments, the whole device 200 may be disposable once the power source is no longer capable of supplying power or once the pressurized container 205 is empty.

Preferably, microprocessor 225 receives instructions from an external controller. Preferably, the external controller is a wireless device. For example the external controller can be a tablet devices, wireless web-enabled or "smart" phone (e.g., Research in Motion's Blackberry™, an Android™ device, Apple's iPhone™) application, other wireless phones, a wearable internet connected device, or a dedicated hand held controller. Preferably, the system is technology agnostic. Communication can occur over any communications network known in the art, including but not limited to wired networks, wireless networks, Zigbee networks, Bluetooth networks, Z-wave networks, WiFi networks, WiMax networks, RF networks, local area networks (LAN), internet networks, wide area networks (WAN), cellular telephone network, 900 MHz wireless networks, and satellite networks. In other embodiments the controller may be directly wired or otherwise coupled to device 200.

Preferably, the external controller is programmed for how to administer the medication (e.g. how often, in what doses, and for how long) and sends signals to the microprocessor as necessary. Additionally, a patient may be able to request a dose on demand. For example, if the patient is experiencing pain or discomfort, the patient may be able to manually activate, push a button, or otherwise indicate to the controller to emit a dose of the medication. In other embodiments, the patient may be able to push a button on device 200 or otherwise directly interact with device 200 to request a dose.

Other embodiments and uses of the invention will be apparent to those skilled in the art from consideration of the specification and practice of the invention disclosed herein. All references cited herein, including all publications, U.S. and foreign patients and patient applications, are specifically and entirely incorporated by reference. It is intended that the specification and examples be considered exemplary only with the true scope and spirit of the invention indicated by the following claims. Furthermore, the term "comprising of" includes the terms "consisting of" and "consisting essentially of." All examples illustrate embodiments of the invention, but should not be viewed as limiting the scope of the invention.

The invention claimed is:

1. An inner ear treatment delivery device, comprising:
a cylindrical pressurized vessel containing a substance;
a control valve within the pressurized vessel;
a flexible seal within the pressurized vessel;
a nozzle directly attached to an outer surface of a first end of the pressurized vessel and in fluid communication with the control valve, wherein the control valve is used to fill the pressurized vessel with the substance and deliver the substance to a patient's inner ear through the nozzle;
a microprocessor adapted to operate the control valve; and
a power source providing energy to the delivery device;
wherein the microprocessor and the power source are coupled externally to a second opposite end of the pressurized vessel; and
wherein the device has a length such that an entirety of the length of the device is capable of being non-invasively insertable and removable from a patient's ear canal without piercing the patient.

2. The device of claim 1, wherein the device is capable of emitting at least one amount of the substance to the patient's inner ear.

3. The device of claim 1, wherein the substance is adapted to diffuse through a patient's ear drum to the patient's inner ear.

4. The device of claim 1, further comprising an external controller in communication with the microprocessor.

5. The device of claim 4, wherein the external controller is one of a smart phone application or a dedicated device.

6. The device of claim 4, wherein the external controller is programmable to control dosage timing and amount.

7. The device of claim 4, wherein the external controller is adaptable to instruct the device to provide a dose on demand.

8. The device of claim 1, wherein the substance is a vapor, a gas, or a liquid.

9. The device of claim 8, wherein the substance is a liquid and the nozzle atomizes the liquid upon emission of the liquid from the device.

10. The device of claim 1, wherein the pressurized vessel is refillable and the nozzle is adapted to receive and emit the substance.

11. The device of claim 1, wherein the device is molded to fit the ear canal.

12. A method of treating an inner ear affliction, comprising:
providing a cylindrical device having a pressurized vessel, a flexible seal within the pressurized vessel, a control mechanism, a nozzle directly attached to an outer surface of a first end of the pressurized vessel, a microprocessor, and a power source, wherein the microprocessor and the power source are coupled externally to a second opposite end of the pressurized vessel;
using the control mechanism to fill the pressurized vessel with a substance through the nozzle;
non-invasively inserting an entirety of a length of the device into a patient's ear canal with the first end of pressurized vessel positioned adjacent to a patient's ear drum; and
instructing the control mechanism to administer at least one amount of the substance to a patient's inner ear through the nozzle.

13. The method of claim 12, wherein the device is non-invasively removable from the patient's ear canal.

14. The method of claim 12, wherein the substance is adapted to diffuse through the patient's ear drum to the patient's inner ear.

15. The method of claim 12, wherein a step of instructing the device to administer at least one amount of the substance to the patient's inner ear is accomplished by an external controller in communication with the microprocessor.

16. The method of claim 15, wherein the external controller is one of a smart phone application or a dedicated device.

17. The method of claim 15, wherein the external controller is programmable to control dosage timing and amount.

18. The method of claim 15, wherein the external controller is adaptable to instruct the device to provide a dose on demand.

19. The method of claim 12, wherein the substance is a vapor, a gas, or a liquid.

20. The method of claim 19, wherein the substance is a liquid and further comprising atomizing the liquid upon emission of the liquid from the device.

21. The method of claim 12, wherein the pressurized vessel is refillable and the nozzle is adapted to receive and emit the substance.

22. The method of claim 12, further comprising molding the device to fit the patient's ear canal.

* * * * *